United States Patent

Fleischfresser

[11] Patent Number: 5,848,892
[45] Date of Patent: Dec. 15, 1998

[54] DEVICE FOR MIXING A DENTAL CERAMICS COMPOSITION

[76] Inventor: Klaus Fleischfresser, Edenbergstrasse 10A, D-70325 Stuttgart, Germany

[21] Appl. No.: 817,680
[22] PCT Filed: Oct. 18, 1995
[86] PCT No.: PCT/DE95/01445
    § 371 Date: May 21, 1997
    § 102(e) Date: May 21, 1997
[87] PCT Pub. No.: WO96/11646
    PCT Pub. Date: Apr. 25, 1996

[30] Foreign Application Priority Data

Oct. 18, 1994 [DE] Germany .............................. 9416738 U
Jul. 27, 1995 [DE] Germany ........................ 195 27 460.1

[51] Int. Cl.$^6$ .................................................. A61C 19/00
[52] U.S. Cl. .......................... 433/49; 269/302.1; 366/602
[58] Field of Search ................................. 433/25, 34, 49; 269/302.1; 366/602; D24/221

[56] References Cited

U.S. PATENT DOCUMENTS 3,756,571  9/1973  Winber ..................................... 366/602
5,529,493  6/1996  Rafetto, Jr. ................................. 433/49

FOREIGN PATENT DOCUMENTS 0005002  10/1979  European Pat. Off. ................. 433/49
2595940   9/1987  France ..................................... 433/49
2640871   6/1990  France ..................................... 433/25
3015410  10/1981  Germany .
9311924  12/1993  Germany .

Primary Examiner—Ralph A. Lewis
Attorney, Agent, or Firm—Karl Hormann

[57] ABSTRACT

A device for mixing a dental ceramics composition is being proposed in which the mixing board (4) consists of a ceramic plate provided with a plurality of parallel channels (7).

9 Claims, 1 Drawing Sheet

DEVICE FOR MIXING A DENTAL CERAMICS COMPOSITION

BACKGROUND OF THE INVENTION

1. Field of the Invention

The invention, in general, relates to a device for mixing a dental ceramics composition and, more particularly, to a device provided with a surface structure upon which a dental ceramics composition may be prepared from two components required for making dental components, such as ceramic crowns or bridges. The two components, water, or a modeling liquid made up chiefly of water, and a ceramics powder are mixed together on a mixing board by a brush or a spatula for subsequent application to a metal frame corresponding in its shape to the part to be produced (e.g. a crown or a bridge) and final firing.

2. The Prior Art

Known apparatus are provided with a mixing board made of glass, a foam material or porous stone. The use of glass mixing boards has proven to be disadvantageous because the dental ceramics composition dries up and hardens very shortly after being mixed together. In order further to process the composition it is necessary repeatedly to moisten it with distilled water until the modeling process has been terminated. By moistening, the composition may become supersaturated with liquid. On the other hand, insufficient moistening may lead to cracks during firing of the dental ceramics composition. Moreover, the constant moistening makes the processing of the dental ceramics composition time-consuming and tedious.

In a known container for storing moist ceramic compositions (DE-A 3,015,410) there are provided recesses which may be covered and in which the dental ceramics compositions may be appropriately stored.

In a known mixing board of the kind under consideration (DE-U 9,311,924), the dental ceramics composition is mixed on a fibrous web, this web being arranged on a mixing board consisting of a ceramic material. The disadvantage of such a device is that the mixing board is foamy or porous so that minute particles present in the mixing liquid may congest the fine pores of the material of the mixing board and may not even be removed by cleaning of the plate. After a certain time so large a number of pores will be congested that the mixing plate is no longer useable and has to be replaced by a new one.

BRIEF SUMMARY OF THE INVENTION

By comparison, the device for mixing of a dental ceramics composition in accordance with the invention offers the advantage of a mixing board made up of a ceramics material provided with a plurality of channels extending in parallel to each other. The mixing board is enclosed by a housing into which the mixing liquid may be filled. Capillary action leads to upward flow of the liquid in the channels so that it reaches the ceramic component placed on the surface of the mixing board. The ceramic powder will absorb no more liquid than is needed for composing the ceramics composition. Supersaturation with liquid cannot occur.

Advantageously, the ceramics composition will maintain the consistency required for modeling over an extended period of time, as any evaporated liquid will be replaced by the mixing liquid rising through the channels. Drying up of the ceramics composition may be prevented even if it remains on the mixing board for some time.

Mechanical mixing of ceramics powder and mixing liquid is avoided since the ceramics powder absorbs the mixing liquid on its own. In this manner, the ceramic composition takes on a dense consistency which advantageously affects the quality and color of the material of the final processed part.

The diameter of the channels is large relative to the grain size of the ceramics powder, relative to dust particles and any particles present in the mixing liquid. Because of the relatively large diameter of the channels they cannot be congested by dust particles, impurities or ceramics powder. The mixing board may be cleaned with water or, in case of strong soiling by a steam jet. By heating in a furnace to temperatures above 1,000° C. any bacteria and spores are destroyed and the board is thus disinfected.

Advantageously, very small quantities of ceramics composition may be mixed on the mixing board. In the event, less ceramics powder and less mixing liquid are needed than when using known mixing boards so that work is rendered efficient and costs may be reduced.

Advantageously, the housing of the mixing board consists of a container and a lid which is either removable from the container or connected to the container for pivotal movement about an axis arranged on the container. The container encloses the mixing board laterally and from below, whereas the lid, when the container is closed, covers the mixing board from above. On the one hand, the housing functions as a reservoir for the mixing liquid. Thus, the container must be tight. On the other hand, the housing protects the mixing board and any ceramics compositions on the mixing board from contamination and mechanical stress.

In accordance with a further advantageous embodiment of the invention, the channels are of square crosssection.

In accordance with a further advantageous embodiment of the invention, the thickness of the intermediate walls between the channels is of small dimension relative to the cross-section of the channels.

In accordance with a further advantageous embodiment of the invention the housing is made of plastic. As compared to other materials, plastic has the advantage of being light and that it can be easily and cost-efficiently manufactured.

In another advantageous embodiment of the invention the housing is made of glass.

In accordance with a further advantageous embodiment of the invention a filter may be placed on the mixing board. To this end, the surface of the mixing board is completely smooth. The use of a filter prevents, among others, the ceramics powder from penetrating into the channels. The ceramics powder is put directly on the filter. On the one hand, the filter prevents the ceramics powder from penetrating into the channels and on the other hand it controls the amount of moisture on the surface of the mixing board.

In accordance with a further advantageous embodiment of the invention the filter is made of paper. Paper filters are cheap and may be replaced after use.

In accordance with a further advantageous embodiment of the invention the filter is made of a textile web, such as, e.g. a cotton web or raw web. Textile filters may be cleaned and reused after cleaning. For cleaning, washing in running water is sufficient.

In accordance with a further advantageous embodiment of the invention a further filter bearing indicia for the mentioned distribution of the composition is arranged between the filter and the mixing board. After terminating the work, the upper filter may be discarded and the lower filter, after drying, may be stored in a patient file to be used again if necessary.

Further advantageous and advantageous embodiments of the invention will become apparent from the ensuing description, drawing and claims.

DESCRIPTION OF THE DRAWINGS

An embodiment of the subject of the invention is shown in the drawing and will be described in more detail hereinafter. In the drawings

DETAILED DESCRIPTION OF PREFERRED EMBODIMENTS

Figure 1:
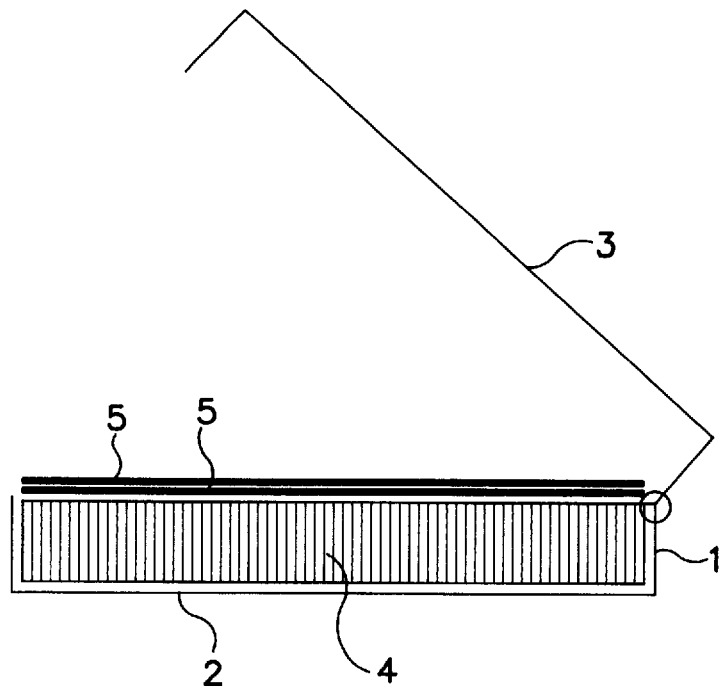
FIG. 1 is a schematic view, in cross-section, of the device in accordance with the invention.

In FIG. 1, there is shown a device in accordance with the invention for mixing a dental ceramics composition.

In FIG. 1, there is shown a housing 1 of substantially rectangular or circular configuration and consisting of a container 2 and a lid 3 schematically shown to be hinged to the container at an upper rim thereof. It will, however, be understood by those skilled in the art that a removable lid such as, for instance, a paint can lid, may be used to equal advantage. The housing may also be of round shape. Within the housing 2, there is disposed the mixing board 4 which is covered from above by a filter 5. As shown, it is also possible to place several, for instance two, filters in superposition. Pencil marks may be put on the lower filter to indicate where certain compositions are to be put on the upper filter. For mixing of a dental ceramics composition, the mixing liquid, e.g. demineralized water, is put into the housing 2 first. The liquid will rise in the channels of the mixing board 4, so that excess water may discarded from the container some time later. Thereafter, the filter 5 is placed on the mixing board 4, and the ceramics powder is applied thereto by a brush a spatula. The liquid rising in the channels penetrates into the ceramics powder so that a modeling ceramics composition will be available after some time.

Figure 2:
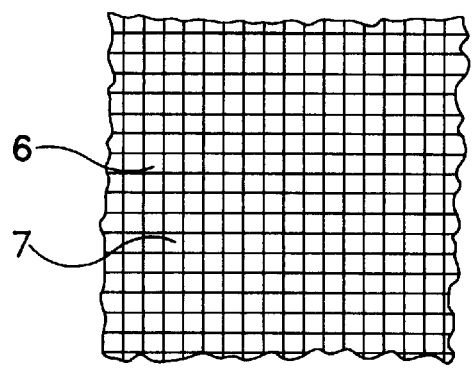
FIG. 2 is a schematic top elevational view, with parts broken away for clarity, of the mixing board in accordance with the invention.

FIG. 2 depicts a section of a mixing board from above. Openings 6 of channels 7 can be recognized. The walls between the channels are relatively thin in order to provide for as many channels in a given surface area as possible. The diameter of the channels is large relative to the ceramics powder particles and dust particles.

All of the elements presented in the description, the ensuing claims and in the drawing may be essential to the invention by themselves as well as in any desired combination.

What is claimed is:

1. A device for preparing a dental ceramics composition from a liquid and a granular ceramics substance, comprising:

means including at least one side wall and a bottom wall for forming a housing having a receptacle therein adapted to contain the liquid;

means opposite the bottom wall for forming a lid for selectively opening and closing the receptacle; and means for forming a substantially flat surface for supporting the granular ceramics substance intermediate the bottom wall and the lid, said surface being perforated by a plurality of open substantially vertical channels closely spaced in substantially parallel relationship for providing capillary flow of the liquid from the receptacle to the granular substance thereby to form the dental ceramics composition.

2. The device of claim 1, wherein the channels are of square cross-section.

3. The device of claim 1, wherein the channels are separated by intermediate walls of small dimension relative to the cross-section of the channels.

4. The device of claim 1, wherein the housing is made of plastic.

5. The device of claim 1, wherein the housing is made of glass.

6. The device of claim 1, wherein at least one liquid-pervious filter may be placed over the channels on the flat surface.

7. The device of claim 6, wherein the filter is made of paper.

8. The device of claim 6, wherein the filter is made of a textile web.

9. The device of claim 6, wherein a further filter is provided between the filter and the flat surface.

\* \* \* \* \*